(12) United States Patent
Holladay et al.

(10) Patent No.: US 6,328,728 B1
(45) Date of Patent: *Dec. 11, 2001

(54) COMPOSITION AND METHOD FOR ENHANCING ELECTROTRANSPORT AGENT DELIVERY

(75) Inventors: Leslie A. Holladay, Mountain View; Lynda G. Treat-Clemons, Cupertino; Patricia Margaret Bassett, Redwood City, all of CA (US)

(73) Assignee: Alza Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/878,002

(22) Filed: Jun. 18, 1997

Related U.S. Application Data

(63) Continuation of application No. 08/341,246, filed on Nov. 17, 1994, now abandoned.

(51) Int. Cl.[7] .................................................. A61M 31/00
(52) U.S. Cl. .................................................. 604/501
(58) Field of Search ........................... 604/20.21, 501; 607/149–153

(56) References Cited

U.S. PATENT DOCUMENTS

| 4,141,359 | 2/1979 | Jacobsen et al. . |
| 4,153,689 | 5/1979 | Hirai et al. . |
| 4,250,878 | 2/1981 | Jacobsen et al. . |
| 4,383,529 | 5/1983 | Webster . |
| 4,474,570 | 10/1984 | Ariura et al. . |
| 4,568,343 | 2/1986 | Leeper et al. . |
| 4,588,580 | 5/1986 | Gale et al. . |
| 4,722,726 | 2/1988 | Sanderson et al. . |
| 4,994,439 | 2/1991 | Longenecker et al. . |
| 5,120,716 | 6/1992 | Miyazawa et al. . |
| 5,250,022 | * 10/1993 | Chien et al. ............................ 604/20 |
| 5,374,241 | * 12/1994 | Lloyd et al. ............................ 604/20 |

FOREIGN PATENT DOCUMENTS

| 2127689A | 4/1984 | (GB) . |
| WO9602232 | 2/1996 | (WO) ................................. A61K/9/00 |

OTHER PUBLICATIONS

Pharmazie, vol. 49, No. 7, Jul. 1994 Eschborn (DE)., pp. 538–529, V.U. Rao et al., "Enhancement of Iontophoretic Permeation of Insulin Across Human Cadaver Skin".
Database WPI, Week 9408, Derwent Publications Ltd., London, GB; AN 94–061979 & JP, A, 06 016 538 (Advance KK et al.), Jan. 25, 1994, See abstract.

* cited by examiner

Primary Examiner—Mark Bockelman
(74) Attorney, Agent, or Firm—Owen J. Bates; D. Byron Miller

(57) ABSTRACT

An electrotransport device (10) for the electrotransport delivery of agents having at least one hydrophobic site thereon, such as peptides and proteins, contains donor and counter electrodes (12, 16 and 14, 18), a power source and electrical control circuitry (24). The donor electrode (12, 16) contains, in addition to the agent, an electrotransport enhancer such as non-ionic surfactants or zwitterionic surfactants without a net charge. A method of increasing electrotransport flux of agent shaving at least one hydrophobic site thereon utilizes non-ionic or zwitterionic surfactants in the solution or suspension containing the agent. A method for the electrotransport delivery of an agent with at least one hydrophobic site through a body surface relies on the incorporation of a non-ionic surfactant or a zwitterionic surfactant without a net charge, into the solution or suspension containing the agent to decrease its hydrophobicity.

10 Claims, 2 Drawing Sheets

COMPOSITION AND METHOD FOR ENHANCING ELECTROTRANSPORT AGENT DELIVERY

RELATED APPLICATIONS

This application is a continuation of application Ser. No. 08/341,246 now abandoned, filed Nov, 17, 1994, and benefit of the filing date of said earlier filed application is claimed under 35 USC §120.

TECHNICAL FIELD

This invention relates to electrotransport agent delivery. More particularly, this invention relates to the electrotransport delivery of agents, such as peptides and proteins, having at least one hydrophobic site. Non-ionic and zwitterionic surfactants are utilized in the present invention to decrease the hydrophobicity of such agents and to enhance their transdermal electrotransport flux.

BACKGROUND ART

Interest in the percutaneous or transdermal delivery of peptides and proteins to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to the binding of hydrophobic sites present on the polypeptides to lipids present in the skin. In addition, polypeptides and proteins are easily degradable during and after penetration of the skin, prior to reaching target cells.

One method of increasing the transdermal delivery of agents relies on the application of an electric current across the body surface or electrotransport. "Electrotransport" refers generally to the passage of a beneficial agent, eg, a drug or drug precursor, through a body surface such as skin, mucous membranes, nails, and the like. The transport of the agent is induced or enhanced by the application of an electrical potential, which results in the application of electric current, which delivers or enhances delivery of the agent. The electrotransport of agents into the human body may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying an electrical pulse, a high voltage pulse, to a membrane. In many instances, more than one of these processes may be occurring simultaneously to different extents. Accordingly, the term "electrotransport", is given herein its broadest possible interpretation, to include the electrically induced or enhanced transport of at least one charged or uncharged agent, or mixtures thereof, regardless of the specific mechanism(s) by which the agent is actually being transported.

Electrotransport devices generally use at least two electrodes which are in electrical contact with some portion of the skin, nails, mucous membranes, or other body surface. One electrode, commonly referred to as the "donor" or "active" electrode, is the one from which the agent is delivered into the body. The other, typically termed the "counter" or "return" electrode, serves to close the electrical circuit through the body. For example, when the agent to be delivered is a cation, ie, a positively charged ion, the anode becomes the active or donor electrode, while the cathode serves to complete the circuit. Alternatively, if an agent is an anion, ie, a negatively charged ion, the cathode is the donor electrode. Both the anode and cathode may be donor electrodes if both anionic and cationic ionic agents are delivered simultaneously. Electrotransport delivery systems generally require at least one reservoir or source of the agent to be delivered to the body. Examples of such donor reservoirs include a pouch or cavity as described in U.S. Pat. No. 4,250,878 to Jacobsen, a porous sponge or pad as described in U.S. Pat. No. 4,141,359 to Jacobsen et al, and a preformed gel body as described in U.S. Pat. No. 4,383,529 to Webster, among others. The pertinent portions of which are incorporated herein by reference. Such donor reservoirs are electrically connected to, and positioned between, the anode or cathode and the body surface, to provide a fixed or renewable source of one or more agents or drugs. In addition, electrotransport delivery systems also typically have an electrical power source, eg, one or more batteries, and an electrical controller designed to regulate the timing, amplitude and/or frequency of the applied electric current, and hence regulate the timing and rate of drug delivery. This power source component is electrically connected to the donor and counter electrodes. Optional electrotransport device components include a counter agent reservoir, adhesive coatings, insulating separation layers, and rate-controlling membranes.

Electrotransport delivery generally increases peptide delivery rates relative to passive or non-electrically assisted, transdermal delivery. However, further increases in transdermal delivery rates and reductions in peptide degradation during transdermal delivery are highly desirable. One method of increasing the agent transdermal delivery rate involves pre-treating the skin with, or alternatively co-delivering with the beneficial agent, a skin permeation enhancer. The term "permeation enhancer" is broadly used herein to describe a substance which, when applied to a body surface through which the agent is delivered, enhances its electrotransport flux. The mechanism may involve a reduction of the electrical resistance of the body surface to the passage of the agent therethrough, an increase in the permeability of the body surface, the creation of hydrophilic pathways through the body surface, and/or a reduction in the degradation of the agent (eg, degradation by skin enzymes) during electrotransport. The term "body surface," as used herein, refers generally to the skin, mucous membranes, and nails of an animal, and to the outer surface of a plant.

The preferred form in which an agent and an enhancer are delivered generally determines the type of delivery system to be used, and vice versa. That is, the selection of a "passive" system which delivers the agent by diffusion or an electrically powered system which delivers the agent by electrotransport will be mostly determined by the form of the agent. For example, with passive delivery systems, it has generally been recognized that the agent is preferably delivered in either its free base or acid form, rather than in the form of a water soluble salt. (eg, U.S. Pat. No. 4,588,580 to Gale et al, at column 3, lines 6–20). On the other hand, with electrotransport delivery devices, it has been recognized that the drug should generally be soluble in water. (eg, U.S. Pat. No. 4,474,570 to Ariura et al, at column 7, lines 5–7). It is generally believed that the pathways for passive and electrotransported transdermal drug delivery are different, with passive delivery occurring through lipid regions, ie, hydrophobic regions, of the skin and electrotransport delivery occurring through hydrophilic pathways or pores such as those associated with hair follicles and sweat glands. Thus, the preferred form of a drug for passive delivery is generally hydrophobic, eg, free base form, whereas the preferred form of a drug for electrotransport delivery is hydrophilic, eg, water soluble salt form.

The form of the permeation enhancer used to enhance transmembrane agent flux is likewise dependent on its mode of delivery. Thus, relatively hydrophobic non-ionic surfactants and organic solvents have been used as passive agent permeation enhancers. U.S. Pat. No. 4,568,343, for example, utilizes poly(ethylene glycol) as a permeation enhancer for passive transdermal delivery. U.S. Pat. No. 4,994,439 to Longenecker et al uses bile salts or fusidates with certain non-ionic detergents for the passive delivery of drugs through nasal mucosal membranes. Similarly, U.S. Pat. No. 4,153,689 discloses the passive nasal administration of insulin with the aid of non-ionic surfactants having a hydrophile-lipophile balance (HLB) of 9 to 22 at a pH from 2.5 to 4.7. U.S. Pat. No. 5,120,716 to Miyazawa et al utilizes a passive percutaneous composition including both an N-containing agent such as non-ionic, amphoteric, semipolar, or cationic surfactants and a non-ionic agent lacking nitrogen atoms. UK Patent 2,127,689 A to Sandoz utilizes benzalkonium chloride and a non-ionic surfactant suitable for use in the nasal mucosa for the passive nasal administration of calcitonin.

On the other hand, relatively hydrophilic permeation enhancers such as ionic surfactants have been used to enhance electrotransport drug delivery. (See, for example, U.S. Pat. No. 4,722,726 to Sanderson et al).

A variety of surfactants have been explored as permeation enhancers for both passive and electrotransport drug delivery. However, the prior art has not recognized a class of permeation enhancers specifically suited for the electrotransport delivery of agents having hydrophobic sites thereon, such as polypeptides or proteins. Thus, there is still a need to provide compositions, which are suitable for increasing the flux of agents having some hydrophobic sites when administered with the aid of an electric current.

DISCLOSURE OF THE INVENTION

The present invention relates to a method of enhancing electrotransport delivery of a beneficial agent (eg, a drug), having at least a certain level of hydrophobicity, through a body surface. An electrotransport delivery device suitable for practicing this method is also provided. In a preferred practice of the method of the present invention, the beneficial agent is a polypeptide with at least said level of hydrophobicity which level of hydrophobicity tends to cause the agent to bind to lipophilic regions encountered upon electrotransport delivery through the body surface.

In accordance with the invention, the beneficial agent is electrotransported in the presence of at least one electrotransport enhancer selected from the group consisting of non-ionic surfactants, zwitterionic surfactants lacking a net charge, and mixtures thereof. The beneficial agent and the enhancer may be provided as a composition contained in a donor electrode reservoir of an electrotransport device. The enhancer is present in the composition in an amount effective to decrease the hydrophobicity of the peptide during electrotransport delivery through the body surface. Surprisingly, relatively hydrophobic surfactants have been found to be best suited to decrease the overall hydrophobicity of certain agents such as polypeptides and proteins, having at least said level of hydrophobicity, and increase agent flux through the body surface during electrotransport delivery. The addition of these relatively hydrophobic surfactants also reduces the biodegradation of agents such as polypeptides and proteins by endopeptidases and other enzymes during their transdermal delivery.

MODES FOR CARRYING OUT THE INVENTION

This invention relates to transdermal electrotransport delivery of somewhat hydrophobic agents, such as drugs and pro-drugs, suitable for the prevention or treatment of disease in humans. The transdermal or transmucosal delivery of these types of agents, and in particular polypeptides and proteins, is in many instances hampered by hydrophobic sites on the agent molecules. These hydrophobic sites tend to interact with (eg, dissolve in) lipophilic regions in body surfaces, such as the skin and mucosa, through which these agents are being delivered. The hydrophobicity of the beneficial agent may be decreased in accordance with this invention, thereby decreasing unwanted interactions between the agent and species (eg, enzymes) present in the body surface during electrotransport delivery and/or increasing the electrotransport flux of the agent. Proper masking of hydrophobic site(s) on the agent being delivered may be attained by reversibly binding or complexing the agent with a non-ionic and/or a zwitterionic surfactant lacking a net charge. The surfactant sufficiently envelopes, and/or helps to reconfigure, the agent to prevent the exposure of its hydrophobic site(s) during electrotransport delivery through the body surface, eg, skin. Once the agent surfactant complex has been delivered through the skin into the underlying tissues and/or the capillary circulation, the surfactant dissociates from the agent, and the agent's original shape and therapeutic characteristics are restored.

The present invention has particular application in the transdermal electrotransport delivery of agents such as polypeptides and proteins. Many polypeptides and proteins have a portion of their molecular structure which can fold into an amphipathic alpha helix, where one face of the helix is hydrophobic and the other is hydrophilic. Typically, the hydrophobic sites on these agents, when delivered transdermally, tend to adversely interact with (eg, dissolve in and/or stick to) lipophilic regions of the body surface (eg, skin, lipids). This interaction impedes the passage of the agent through the skin or other body surface, and reduces overall agent flux. The non-ionic and zwitterionic surfactants of this invention shield the hydrophobic site(s) on the agent and thus prevent these interactions with lipophilic regions of the body surfaces.

The hydrophobicity of an agent (eg, an agent such as a polypeptide or protein in solution, as well as the relative increase or decrease thereof) is determined by passing the agent-containing solution through a chromatography column filled with a particular "hydrophobic interaction" bead material and measuring either (1) the time required for the agent to elute (ie, pass through) the column or (2) the volume of liquid (ie, the same liquid used in the agent-containing sample, but with the agent removed) required to be pumped through the column in order to elute the agent. For the purposes of the present invention, the hydrophobicity of an agent is defined in terms relative to the marker compound, N-acetyl tryptophanamide (sold by Sigma Chemical, St. Louis, Mo.), which has a somewhat moderate hydrophobicity. Hydrophobicity, as that term is used herein, is measured using a 5 mm diameter glass column having a length of 5 cm (ie, column volume of 1.0 mL) and packed with cross-linked agar beads having an average particle size of 13.5 µm. Examples of suitable hydrophobic bead materials include cross-linked agar gel beads (Superose 12) having hydrophobic ligands attached to the agar via chemically stable ether linkages ((Superose 12)—O—$CH_2$—CHOH—$CH_2$—O—R) such as alkyl-Superose wherein R is —$CH_2$—$C(CH_3)_3$ and phenyl-Superose wherein R is phenyl, both of which are sold in pre-packaged column form by Pharmacia Biotech, Inc. of Piscataway, N.J. Immediately downstream from the column is placed a flow cell which permits continuous UV absorbance measurements of the solution flowing out of the column. Suitable flow cells and UV absorbance detectors are sold by Perkin-Elmer Corp., Applied Biosystems, Foster City, Calif. Hydrophobicity measurements are conducted at 32° C. with the same buffer that is used in the electrotransport system which is used to deliver the agent (eg, transdermally) to the patient. The buffer strength used in the hydrophobicity measurements is 10 mM ionic strength. The term "certain hydrophobicity" as used herein, means that the time required for the agent to elute from the column, relative to the time required for N-acetyl tryptophanamide to elute, is as follows:

$$t_a/t_m > 0.7, \text{ and preferably } t_a/t_m > 3$$

wherein;

$t_a$ is the time at which the peak UV absorbance value is recorded for the beneficial agent in the flow cell, less the time required to initially fill the column with the agent-containing solution (ie, dead volume retention time); and $t_m$ is the time at which the peak UV absorbance value is recorded for the N-acetyl tryptophanamide marker in the flow cell, less the time required to initially fill the column with the marker-containing solution (ie, dead volume retention time).

The above described measurement of agent hydrophobicity is substantially independent of column size and flow rate through the column.

In addition to hydrophobicity, the following analytical techniques are described and used herein;

(1) measurement of the three-dimensional shape or ellipticity of the agent (eg, a polypeptide or protein) by circular dichroism spectroscopy; and (2) measurement of the mobility of an agent (eg, a polypeptide or protein) in a liquid-containing medium under the influence of an applied electric field (ie, the electrophoretic mobility of the agent);

The composition of the present invention (ie, the agent and the surfactant combined) preferably exhibits a molar ratio of surfactant:agent in the range of about 3 to 10 in order to achieve agent electrotransport fluxes above about 1 µg/$cm^2$·hr. Similarly, the composition of this invention also preferably exhibits an electrophoretic mobility of about $1 \times 10^{-5}$ $cm^2$/V·sec, and up to about $5 \times 10^{-4}$ $cm^2$/V·sec, and greater, and more preferably greater than about $0.75 \times 10^{-4}$ $cm^2$/V·sec and greater, to reach drug fluxes of about 1 µ/$cm^2$·hr and greater, and up to about 20 µg/$cm^2$·hr. Although ellipticity values give an indication of the amount of surfactant binding, they are highly dependent on the particular agent being delivered. Generally speaking, a mean residue ellipticity value lower than about –9000 is preferred, although values of about –6,000 to –30,000 are within an acceptable range. Therefore, a most preferred composition for the electrotransport delivery of the agent has an HIC elution volume of less than about 4 column volumes and an electrophoretic mobility of more than about $1.0 \times 10^{-5}$ $cm^2$/V·sec, and as high as about $1 \times 10^3$ $cm^2$/V·sec. However, the actual electrotransport flux of the agent clearly depends on a wide range of parameters, including the particular electrotransport delivery conditions (eg, current density) used and the characteristics of the agent and the body surface, and other conditions which may vary on any given delivery application. Thus, the prior ranges are offered merely as guidelines, but are not intended to be limiting for any specific agent and electrotransport enhancer combination.

As used herein, the term "non-ionic surfactant" is defined as a surfactant which has hydrophobic and hydrophilic portions, but lacks charged groups. Non-ionic surfactants suitable for use in the present invention include, but are not limited to, polyoxyethylenes such as TWEEN® 20 (polyoxyethylene (20) sorbitan monolaurate), TWEEN® 40 (polyoxyethylene (20) sorbitan monopalmitate), TRITON® X-100 and TRITON® X-114; alkyldimethylamine oxides, such as dodecyldimethylamine oxide, at pH above 6; alkyl glucosides, such as decyl-β-D-glucopyranoside, nonyl-β-D-glucopyranoside, octyl-β-D-glucopyranoside, heptyl-β-D-glucopyranoside, hexyl-β-D-glucopyranoside; alkyl maltosides, such as dodecyl-β-D-maltoside and decyl-β-maltoside; alkyl thioglucosides, such as octyl-β-D-thioglucopyranoside and heptyl-β-D-thioglucopyranoside; Big CHAP series species, such as deoxyBigCHAP and BigCHAP; CHAPSO; digitoxin; glucamides, and mixtures thereof. Preferred non-ionic surfactants for the present invention are TWEEN® 20 and TWEEN® 40.

The term "zwitterionic surfactants", as used herein, refers to surfactants having charged groups, but lacking overall net charge. Although many zwitterionic surfactants may display an ionic character at a certain pH, the zwitterionic surfactants are in accordance with the present invention preferably employed at a pH in which the overall charge on the zwitterionic surfactant is zero. Preferred zwitterionic surfactants according to the present invention include, without limitation, the following.

TABLE 1

Exemplary Zwitterionic Surfactants

| Zwitterionic Surfactant | pH Range |
| --- | --- |
| Acyl carnitines such as:<br>Palmitoyl (hexadecyl) carnitine<br>Myristoyl (tetradecyl) carnitine<br>Lauryl (dodecyl) carnitine | about 6 to 8 |
| N-alkyl-N,N-dimethyglycines such as:<br>N-dodecyl-N,N-dimethylglycine<br>N-tetradecyl-N,N-dimethylglycine<br>N-hexadecyl-N,N-dimethylglycine | above about 6 |
| Lysolecithins such as:<br>Lauryl lysolecithin<br>Myristoyl lysolecithin | above about 4 |

TABLE 1-continued

Exemplary Zwitterionic Surfactants

| Zwitterionic Surfactant | pH Range |
| --- | --- |
| Palmitoyl lysolecithin | |
| Alkyl sulfobetaines such as: | any pH |
| N-dodecyl sulfobetaines | |
| N-tetradecyl sulfobetaines | |
| N-hexadecyl sulfobetaines | |
| Zwitterionic bile salts and derivatives such as: | any pH |
| CHAPS and CHAPSO Glucamides | |
| alkyl Glucosides | |
| alkyl thioglucosides | |
| alkyl maltosides | |

The zwitterionic bile salts and derivatives thereof are known in the art and need not be described in detail herein. For example, CHAPS, CHAPSO, and similar compounds which are listed in the CalBiochem Catalogue (1994) may be used as a zwitterionic surfactant as described herein.

The electrotransport enhancer is preferably present in an amount of about 0.1 to 30 wt % of the composition, and more preferably about 10 to 20 wt % thereof. In a preferred embodiment, the composition of this invention further comprises a lower alkanol or diol, eg, a $C_2$–$C_{10}$ alkanol or alkanediol, more preferably ethanol or dodecanediol, in an amount of about 0.1 to 10 wt % of the composition. In another preferred embodiment, the composition of the present invention also comprises water in an amount of about 1 to 90 wt % thereof. The composition of the invention may optionally include one or more additives such as binders, buffers, anti-oxidants, preservatives, solvents, anti-fungal or antibacterial agents, and the like, as is known in the art for iontophoretic delivery compositions.

One method of measuring the hydrophobicity of an agent such as a polypeptide or protein is by hydrophobic interaction chromatography (HIC). The principles and conditions associated with HIC are fully described in Protein Purification: Principles, High Resolution Methods, and Applications, Janson and Ryden, Eds., pp. 207–226 (1989), the pertinent portions of which are incorporated herein by reference. This method requires passing a composition through a hydrophobic interaction column and measuring the volume of solvent required for its complete elution. The hydrophobic sites on the agent are generally attracted to hydrophobic groups, such as aryl groups, affixed to beads placed within the column. A preferred HIC column material is phenyl-superose (Pharmacia, Sweden), a cross-linked polysaccharide which has been covalently modified to have pendant hydrophobic aryl groups. These pendant groups are similar to the hydrophobic or lipophilic species in the skin layers. Thus, this hydrophobic interaction column approximates, and is a good in vitro model for, an animal's skin layer as a barrier to transport of a polypeptide or protein. Therefore, HIC elution, volumes or retention times may be used to predict relative transdermal electrotransport delivery rates of agents having hydrophobic sites.

Ellipticity is a relative measure of the three-dimensional shape or conformation of a polypeptide chain. Ellipticity measurements may be obtained experimentally from circular dichroism (CD) spectroscopy as described by J. T. Yang et al, Methods in Enzymology 130: 208–269 (1986); R. W. Woody et al, p.p. 16–114, in The Peptides: Analysis, Synthesis, Biology, ed. S. Udenfriend & J. Meienhofer, Academic Press, N.Y. (1985); and W. Curtiss Johnson, Jr. et al, Ann. Rev. Biophys. Chem. 17:145 (1988), the pertinent portions of which are incorporated herein by reference. For example, a fully alpha-helical protein would have an ellipticity of about –32,000 degree-cm$^2$/decimole while a randomly coiled polypeptide chain would have an ellipticity of about –2000 deg-cm$^2$/dmol. Hydrophobic side chains of randomly coiled polypeptide chains having an ellipticity near –2000 deg-cm$^2$/dmol, tend to separate from one another so that no significant area of hydrophobic character exists. In contrast, polypeptides tightly coiled in an alpha-helical conformation and having an ellipticity near –32,000 deg-cm$^2$/dmol, display many overlapping hydrophobic side chains. This high concentration of hydrophobic side chains creates an area of substantial hydrophobic character which has a tendency to bind to non-ionic and zwitterionic surfactants. Given that the numerous conformations of an agent, such as a polypeptide are in equilibrium, the transdermal electrotransport enhancer binding of hydrophobic sites on alpha-helical conformations will shift the equilibrium, resulting in higher ellipticity values. Thus, in most cases, higher ellipticity values provide a relative measure of increased binding of hydrophobic sites by the electrotransport enhancer, which translates into an increased electrotransport agent flux.

Electrophoretic mobility is based upon the steady state rate of motion of ions under an applied electrical field, and the velocity of an ion under these conditions is generally directly proportional to the applied voltage. The proportionality constant, defined as the electrophoretic mobility of a chemical species, is generally dependent upon the average charge, size and shape of the chemical species and the properties of the solvent. Electrophoretic mobility measurements can be obtained from a capillary electrophoresis apparatus. Thus, capillary electrophoresis may also be used to estimate the relative agent delivery rate through a body surface, such as skin, by electrotransport. The use of capillary electrophoresis is discussed by W. G. Kuhr et al, Capillary Electrophoresis, Analytical Chem. 64: 389–407 (1992); A. C. Rickard et al, Analytical Biochem. 197: 197–207 (1991), the relevant portions of which are incorporated herein by reference.

This invention is useful in the delivery of agents such as drugs or pro-drugs having at least a certain hydrophobicity, defined by $t_a/t_m$ being greater than 0.7 and preferably greater than 3, including peptides, polypeptides and proteins. This includes agents within a broad class normally delivered through the body surfaces and membranes, including skin, mucosa and nails. As used herein, the expression "agent" is intended to have its broadest interpretation as any substance, such as a drug or pro-drug, which is delivered to a living organism or plant to produce a desired effect. In general, this includes therapeutic agents in all of the major therapeutic areas including, but not limited to, anti-infectives such as antibiotics and antiviral agents; analgesics and analgesic combinations; anesthetics; anorexics; anti-arthritics; anti-asthmatic agents; anti-convulsants; antidepressants; anti-diabetic agents; anti-diarrheals; anti-histamines; anti-inflammatory agents; anti-migraine preparations; anti-motion sickness preparations; anti-nauseants; anti-neoplastics; anti-parkinsonism drugs; anti-pruritics; anti-psychotics; antipyretics; antispasmodics including gastrointestinal and urinary; anticholinergics; sympathomimetics; xanthine derivatives; cardiovascular preparations including calcium channel blockers; beta-agonists; beta-blockers; anti-arrythmics; anti-hypertensives; ACE inhibitors; diuretics; vasodilators including general, coronary, peripheral and cerebral vasodilators; central nervous system stimulants; cough and cold preparations; decongestants; diagnostics; hormones such as parathyroid hormones; hypnotics; immunosuppressives; muscle relaxants; parasympatholytics; parasympathomimetics; prostaglandins; proteins; peptides; psychostimulants; sedatives and tranquilizers.

The invention is particularly useful in the controlled delivery of peptides, polypeptides, proteins, or other macromolecules having a certain hydrophobicity, defined by $t_a/t_m$ being greater than 0.7 and preferably greater than 3. These macromolecular compounds have to date proven difficult to deliver transdermally or transmucosally by electrotransport because of their size and hydrophobic character. These macromolecular substances typically have a molecular weight of at least about 300 Daltons, and more typically, about 300 to 40,000 Daltons. Examples of peptides and proteins which may be delivered using the composition and device of the present invention include, without limitation, LHRH, LHRH analogs such as buserelin, gonadorelin, naphrelin and leuprolide, GHRH, GHRF, calcitonin, insulin, insulinotropin, heparin, calcitonin, octreotide, endorphin, TRH, NT-36 (chemical name: N-[[(s)-4-oxo-2-azetidinyl] carbonyl]-L-histidyl-L-prolinamide], liprecin, pituitary hormones (eg, hGH, hFSH, hLH, desmopressin acetate), follicle luteoids, (α-ANF, growth factor releasing factor (GFRF), β-MSH, somatostatin, bradykinin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta. Polypeptides preferred for use with the present invention are those polypeptides having a substantial hydrophobic character, such as for example, insulin, calcitonin, and derivatives thereof.

The pH of the compositions may have a significant impact on the electrotransport delivery rate of the agent, particularly when the agent is a peptide or a protein since the charge, character and conformation of a polypeptide are often pH dependent. Iontophoresis, the delivery of the hydrophobic agent in an ionized form, is the preferred method of electrotransport according to this invention. Since iontophoresis requires ionized species, the pH of the composition is preferably chosen so that the agent is in an ionized state. This can be accomplished by maintaining the pH of the protein or peptide-containing solution at least 1 and preferably at least 2 pH units away from the isoelectric pH of the protein or peptide. For instance, the electrotransport delivery of an agent such as insulin is preferably conducted at a pH of about 2.5 to 4, where insulin displays an overall positive charge, or at a pH of about 8 to 10, where insulin displays an overall negative charge. However, as discussed earlier, if a zwitterionic surfactant is used, the pH is preferably such that the surfactant displays no net charge. Thus, the preferred pH range for electrotransport delivery of a polypeptide is dependent upon the properties of the chosen agent and surfactant.

Figure 1:
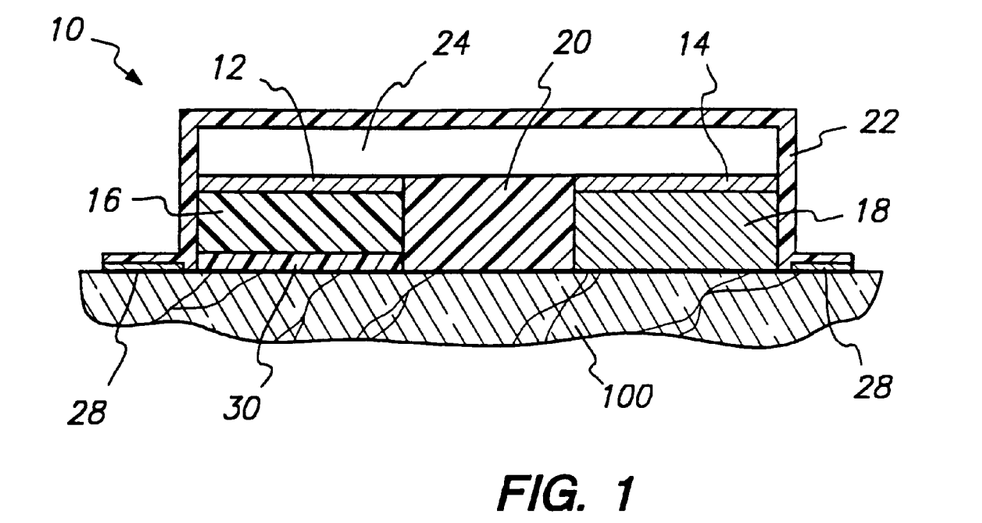
FIG. 1 shows a sectional view of one embodiment of an electrotransport device in accordance with the present invention.

The composition of the present invention is suitable for use in a wide variety of electrotransport devices. One example of an electrotransport drug delivery device which may be used with the present invention is designated by reference numeral 10 and is illustrated in FIG. 1. Device 10 has two current conducting members, referred to herein as a donor electrode 12 and a counter electrode 14. The electrodes 12 and 14 may be composed of an electrically conductive material such as a metal. For example, the electrodes 12, 14 may be formed from metal foil, metal screen, metal deposited or painted on a suitable backing, such as by calendaring or film evaporation, or by mixing a metal powder in a binder matrix. Examples of suitable metals include silver, zinc, silver chloride, aluminum, platinum, stainless steel, gold, and titanium. Most preferably, the anodic electrode is comprised of silver, while the cathodic electrode is comprised of silver chloride. Silver is preferred as an anode over other metals because of its relatively low toxicity to humans. Silver chloride is preferred as a cathode because the reduction of silver chloride produces chloride ions which are endogenous to the human body. Alternatively, the electrodes may be formed of a polymer matrix containing a conductive filler such as a metal powder, powdered graphite, carbon fibers, or other electrically conductive filler material. The polymer-based electrodes may be produced by mixing the conductive filler, eg, silver or silver chloride, in a polymer matrix.

The donor and counter electrodes 12 and 14 are positioned adjacent to the donor reservoir 16 and the counter agent reservoir 18, respectively. The donor reservoir 16 contains the agent to be delivered, while the counter reservoir 18 typically contains a biocompatible electrolytic salt. The donor reservoir 16 and optional counter agent reservoir 18 may be any material adapted to absorb and hold a sufficient quantity of liquid therein in order to permit transport of agent therethrough by electrotransport. For example, gauzes, pads or sponges composed of cotton or other absorbent fabric, both natural and synthetic, may be used. More preferably, the matrices of the reservoirs 16 and 18 are composed, at least in part, of a hydrophilic polymer material. Hydrophilic polymers are preferred because water is the preferred ion transport medium, and hydrophilic polymers have a relatively high equilibrium water content. Most preferably, the matrices of the reservoirs 16 and 18 are solid polymer matrices composed, at least in part, of insoluble hydrophilic polymer. Insoluble hydrophilic polymer matrices are preferred for structural reasons over soluble hydrophilic polymers.

The matrices can be cross-linked with the agent components in place such as a silastic matrix, or the polymers can be prefabricated and sorbed with the components from solutions as is the case with cellulose, woven fiber pads and sponges. The agent reservoirs 16 and 18 can alternately be a gel matrix structure, formed similarly to the polymeric matrix structure, wherein the gel is formed of a hydrophilic polymer which is swellable or soluble in water. Such polymers may be blended with the components in any ratio, but preferably represent from a few to about 50 wt % of the reservoir. The polymers may be linear or cross-linked. Suitable hydrophilic polymers include co-polyesters such as HYTREL (DuPont De Nemours & Co., Wilmington, Del.), polyvinylpyrrolidones, polyvinyl alcohol, polyethylene oxides such as POLYOX (Union Carbide Corp.), CARBOPOL (BF Goodrich of Akron, Ohio), blends of polyoxyethylene or polyethylene glycols with polyacrylic acid such as POLYOX blended with CARBOPOL, polyacrylamide, KLUCEL, cross-linked dextran such as SEPHADEX (Pharmacia Fine Chemicals, AB, Uppsala, Sweden), WATER LOCK (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxylethyl methacrylate (National Patent Development Corp.), natural gums, chitosan, pectin, starch, guar gum, locust bean gum, and the like, along with blends thereof. This list is merely exemplary of the materials suited for use in this invention, and other suitable hydrophilic polymers can be found in Scott and Roff (Scott, J. R., & Roff, W. J., Handbook of Common Polymers, CRC Press (1971), the pertinent portions of which being hereby incorporated by reference). The matrices of the reservoirs 16 and 18 may optionally contain a hydrophobic polymer for enhanced structural rigidity. Preferably the hydrophobic polymer is heat fusible, in order to improve the lamination of the reservoirs to adjacent components, such as the insulator 20 shown in FIG. 1. Suitable hydrophobic polymers for use in the reservoir matrices include, but are not limited to, polyisobutylenes, polyethylene, polypropylene, polyisoprenes and polyalkenes, rubbers, copolymers such as KRATON, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol, isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched alkyl maleamic acids wherein the alkyl group has 10–24 carbon atoms, glycol diacrylates, and blends thereof. Most of the above-mentioned hydrophobic polymers are heat fusible. The reservoir matrices may be a polymeric matrix structure formed by blending the desired agent, electrolyte, or other component(s), with an inert polymer by such processes as melt blending, solvent casting, or extrusion. The counter reservoir 18 may contain any one or more of the following electrolytes: alkali metal salts such as NaCl; alkaline earth metal salts such as chlorides, sulfates, nitrates, carbonates, and phosphates; organic salts such as ascorbates, citrates, and acetates; electrolytes containing redox species such as $Cu^{-2}$, $Fe^{-2}$, $Fe^{-3}$, quinone, hydroquinone, $Ag^{-2}$ and $IO_3^-$; and other biocompatible salts and buffers. Sodium chloride is the preferred electrolytic salt for the counter reservoir 18. In addition to the agent to be delivered and electrolyte, the reservoirs 16 and 18 may also contain other conventional materials such as dyes, pigments, inert fillers, and the like.

The donor electrode 12 and donor reservoir 16 are separated from the counter electrode 14 and counter reservoir 18 by an electrical insulator 20 which prevents electrical shorting. The insulator 20 prevents direct ion transport, ie, short-circuiting, between the donor reservoir 16 or the donor electrode 12 and the counter electrode 14 or optional counter reservoir 18. Given the purpose of the insulator, insulator 20 is preferably made of a hydrophobic material which is impermeable to the passage of both ions and electrons. Preferably, the insulating material is a material capable of strong bonding with the reservoir polymers, thereby providing further overall structural integrity for the device. Preferred insulating materials include poly(isobutylenes) and ethylene vinyl acetates (EVA).

The device 10 also has a backing layer 22 composed of a water-proof and preferably electrically insulating material. In addition, the backing layer 22 may provide some structural integrity to the device.

Electrical power may be supplied by a current generating and control circuit, shown schematically in FIG. 1 as a layer 24, which may include one or more batteries. One or more 3 volt button cell batteries, such as PANASONIC® model CR 2025, are suitable to power device 10. If the counter and donor electrodes are of dissimilar metals or have different half cell reactions, it is possible for the system to generate its own electrical power. Typical materials which provide a galvanic couple include a zinc donor electrode and a silver chloride counter electrode. Such a combination will produce a potential of about one volt. There exist numerous other examples of galvanic couple systems potentially useful in the present invention. Standard electrochemical reactions and the respective reduction potentials are well known in the art. (see, eg, CRC Handbook of Chemistry and Physics, pp. D133–D138, $62^{nd}$ edition (1981–1982), which is incorporated herein by reference). The power source in layer 24 is in electrical contact with the electrodes 12 and 14 such that each of the electrodes 12, 14 is electrically connected to the opposite pole of the power source in layer 24. Layer 24 may also include electronic circuitry for controlling the operation of the electrotransport device. Thus, layer 24 may include circuitry designed to permit the patient to manually turn the system on and off, such as with an on-demand medication regime, or to turn the system on and off at some desired periodicity, for example, to match the natural or circadian patterns of the body. A relatively simple controller or microprocessor can control the current as a function of time or can generate complex current wave forms such as pulses or sinusoidal waves. The control circuitry may also include a biosensor and some type of feedback system which monitors biosignals, provides an assessment of therapy, and adjusts the drug delivery accordingly.

The device 10 adheres to the body surface 100 in this embodiment by means of a peripheral adhesive layer 28. An optional passive flux control membrane 30 is positioned between the body surface 100 and the donor reservoir 16, respectively.

The device 10 may additionally contain other features, such as a removable protective liner (not shown) on the body surface contacting face of the device. Furthermore, certain components in device 10 are unnecessary or optional. Counter reservoir 18 is one example of an optional component. Also, if electrodes 12 and 14 are chosen such that a galvanic couple exists, an independent power source, eg, one or more batteries, in layer 24 may be an optional component. Thus, device 10 of FIG. 1 is provided solely for illustration of one example of an electrotransport delivery device which may be used with the compositions of the present invention.

Having generally described the invention, the following examples will illustrate how variations of the previously described parameters provide means for delivering by electrotransport therapeutic beneficial agents having at least a certain level hydrophobicity.

EXAMPLES

Measurement of In Vitro Transdermal Flux

A. Preparation of Human Skin Samples

Human cadaver skin was prepared by first removing about 1 mm thick skin samples in the form of strips. The skin strips were placed in polyethylene bags, sealed and placed in a refrigerator at about 4° C. for temporary storage. Prior to use in the electrotransport cell, the skin strips were placed in one-liter beakers containing water at 60° C. for about 90 seconds with gentle stirring. Then, the skin strips were removed and placed onto the absorbent side of a piece of BENCHKOTE™ material with the dermis side down. Using flat tipped tweezers to retain the dermis, the epidermis was removed from each strip with a round-tip spatula. Each epidermis, stratum corneum side up, was transferred to a PYREX™ glass tray filled with water. Each floating epidermis was stretched essentially flat. After removal from the water 2.22 cm (⅞ in) diameter disks of each epidermis were punched out of areas having negligible surface damage. The discs were stored at 4° C. in a sealed container with water droplets to maintain their moisture.

B. Set-up of Electrotransport Cell and Composition

Figure 2:
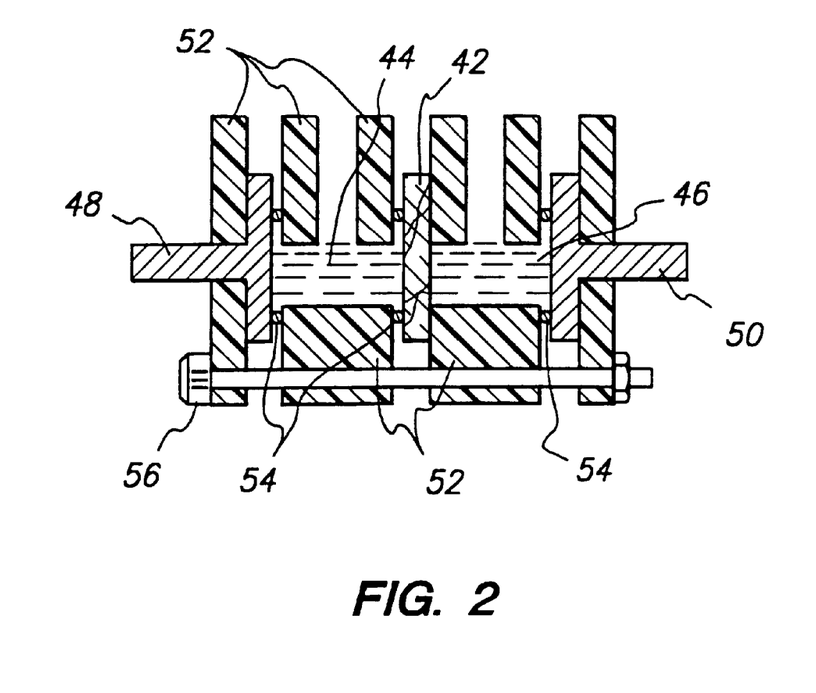
FIG. 2 shows a sectional view of an electrotransport flux testing cell.

The human cadaver epidermis disks were mounted between the donor compartment 44 and the receptor compartment 46 of a two-compartment permeation cell, shown in FIG. 2. The permeation cell was comprised of a polycarbonate support structure 52, having O-ring seals 54, which was held together with a stainless steel bolt and nut 56. The human cadaver epidermis disks 42 were mounted with the stratum corneum side facing the donor compartment 44. A silver anode 48 was placed adjacent to the donor compartment 44, and a silver chloride cathode 50 was placed adjacent to the receptor compartment 46. The area of the skin disk 42 exposed for transport was about 1.26 cm² and the volume of each of compartments 44 and 46 was about 2 mL. The electrodes 48, 50 were electrically connected to a galvanostat (not shown in FIG. 2), which was set to apply the voltage necessary to achieve a constant predetermined level of electric current, ie, 100 $\mu A/cm^2$.

The solution concentration of the polypeptide in the donor compartment 44 was, unless otherwise specified, 1 mM. The pH of the solution in the donor compartment 44 was maintained, unless otherwise specified, at about pH 6–7 using 10 mM histidine buffer. Dulbecco's phosphate buffered saline (about 0.15N NaCl with minor amounts of other ions, pH 7.0) was placed in the cathodic receptor compartment 46. The temperature of the cell was maintained at 32° C. The polypeptide flux was determined by periodic sampling of the solution in the receptor compartment 46.

Measurement of Circular Dichroism

In general, the structure of a polypeptide in an aqueous buffered solution is in constant flux between portions thereof being random coil and alpha-helix configurations. For the polypeptides used in the following examples, the predominant structure is a random coil since the alpha-helix configuration is unstable in the absence of bound surfactant. According to the present invention adding surfactant to an aqueous solution of a polypeptide stabilizes the alpha-helix configuration. Circular dichroism is a measurement of the amount of the alpha-helix configured polypeptide present in the solution. Thus, circular dichroism provides an indirect measurement of the degree of binding of the surfactant to the polypeptide. (See, for example, Epand R. M., Epand R. F., Orlowski R. C., Schuleter R. J., Boni L. T. and Hui S. W., Biochemistry 22, 5074–5084 (1983); Hui, S. W., Epand R. M., Dell K. R., Epand R. F. and Orlowski R. C., Biochimica Biophysica Acta 772, 264–272 (1984); Epand R. M., Epand R. F., and Orlowski R. C., International Journal Peptide Protein Research 25 105–111; Epand R. M., Epand R. F., Orlowski R. C., Seyler J. K. and Colescott R. L., Biochemistry 25, 1964–1968; Epand R. M., Seyler J. K. and Orlowski R. C., European Journal Biochemistry 159, 125–127 (1986); Wiersema P. H., Loeb A. L. and Overbeek, J., Colloid Interface Science 22, 78–99 (1966)).

The surfactant/peptide circular dichroism (CD) spectra were obtained in a 2 mm path-length cell (110-Q-2 Model, AVIV, Lakewood, N.J.) at 32° C. The cell was initially loaded with 0.60 mL of a solution containing about 0.25 mg/mL of the peptide in 10 mM sodium chloroacetate (pH 3.5) or 10 mM sodium borate (pH 9.0). The buffers were selected to minimize the effect of the temperature on the pH of the solution and to minimize light absorption, thereby optimizing the signal-to-noise ratio (SNR). The peptide concentration was determined by spectrophotometry, with log-log correction for light scattering. The surfactant concentration was increased step-wise by titration of concentrated surfactant stock directly into the CD cell, followed by eight inversions of the cell, with the air bubble providing the mixing turbulence. After mixing, the cell was placed into the AVIV 62 CD spectrometer (AVIV, Lakewood, N.J.). In order to approximate temperature and chemical equilibrium, the sample remained in the spectrometer 5 minutes before a reading was taken. The CD spectrum was taken using a band pass of 1 nm, a data interval of 1 nm, and a data averaging time of 10 seconds. The mean residue ellipticity is the ellipticity divided by the path length in cm times the amino acid residue concentration in decimoles/cm³. See Methods in Enzymology, Vol 130, pp 208–269, Yang et al, "Calculation of Protein Conformation from Circular Dichroism" (1986).

Measurement of Hydrophobicity

Since transdermal electrotransport drug delivery has been shown to occur mainly through hydrophilic shunt pathways (eg, sweat ducts and hair follicles), the hydrophobicity of the drug/agent being delivered is predictive of suitability for transdermal electrotransport delivery. The less hydrophobic the drug/agent, the better is the anticipated transdermal electrotransport flux. Hydrophobicity measurements were conducted by passing the peptide/surfactant mixtures through a high performance liquid chromatography column, model C-R4A Chromatopac (Shimadzu Instruments, Pleasanton, Calif.), which included a 5 mm×5 cm phenyl Superose column (Pharmacia Biotech, Inc., Piscataway, N.J.), a SCL-6A pump flow rate controller, an SPD-6AV UV absorbance detector and an LC-6A pump. The column temperature was maintained at 32° C. with an ALLTECH 330 column heater (ALLTECH, Deerfield, Ill.). The dead volume retention time was 2 minutes. Injections (50 $\mu L$) were made using a Rheodyn injector and Hamilton syringes. The HIC analysis conditions were 0.5 mL/min flow rate, absorbance of 0.002, UV detection at 214 nM, and attenuation of 5. All buffers were filtered through a 0.4$\mu$ filter and degassed before use.

Measurement of Electrophoretic Mobility

Since electrophoretic mobility (ie, the ability of a drug/agent to migrate in an electric field) is an important aspect of electrotransport drug delivery, the electrophoretic mobility of the drug/agent being delivered is predictive of suitability for transdermal electrotransport delivery. Electrophoretic mobility measurements were performed using a capillary zone electrophoresis instrument (model 2100 P/ACE instrument, Beckman Instruments, Inc., Palo Alto, Calif.). At acid pH values DB-WAX, DB-1, DB-17 (J&W Scientific, Folsom, Calif.) capillary columns were used either with 50 or 100 micron internal diameter column and CElect H75 (Supelco, Bellefonte, Pa.) capillary column with a 75 micron internal diameter. At alkaline pH values uncoated silica capillaries of length 57 cm with an internal diameter of 75 microns were used with an applied voltage of 20 kV. If any electroosmotic flow was present, it was detected using a neutral marker such as 0.01% benzyl alcohol (SIGMA, St. Louis, Mo.) or 1/500 mesityl oxide (Applied Biosystems, Foster City, Calif.). The optimum voltage was determined by doing an Ohm's Law test on each buffer and capillary system. The temperature of the capillary columns was set at 32° C. and a two second pressure injection was done. A UV detector was used to monitor peptide and markers at either 214 or 280 nm.

To determine any obvious interaction between the peptide and the internal capillary wall for the coated capillaries, a DB-WAX column with a 0.05µ internal diameter with varying total lengths of 57, 47, 37, 27 cm (hence, the varying lengths to detector were 50, 40, 30, and 20 cm, respectively) was used. Voltage injection had to be used for the 27 cm length column. The voltage applied varied depending on the capillary length.

The following equation was used to determine electrophoretic mobility $\mu$.

$$\mu = \frac{\text{Total Capillary Length (cm)} \times \text{Length to Detector (cm)}}{\text{Voltage (V)} \times \text{Migration Time (sec)}}$$

If the electroosmotic flow is detected, the following equation can be used.

$$\mu_{peptide} = \mu_{total} - \mu_{neutral\ marker}$$

Example 1

Effect of Non-ionic Surfactant on Protein Electrophoretic Mobility, Ellipticity and HIC Retention Time The measurement procedures described above were conducted on an aqueous solution of the protein insulinotropin, with TWEEN® 20 (MW=1126 g/mol) as the surfactant, with the following modifications. The insulinotropin donor solution concentration was 0.12 mg/mL. One test was run in 10 mM sodium borate at pH 9.0 and another test in 10 mM sodium chloroacetate at pH 3.5. The results are shown in Tables 2 and 3 below.

Table 2 shows the ellipticity and electrophoretic mobility as a function of TWEEN® 20 concentration at pH 9.0 in 10 mM sodium borate while Table 3 lists similar data for pH 3.5 and 10 mM sodium chloroacetate. Fractional changes (%δ) are defined as the difference between the reading at a given surfactant concentration ($E_c$) minus the reading at zero surfactant ($E_0$), the quantity divided by the difference between the reading at saturated surfactant concentration ($E_s$) minus the reading at zero surfactant ($E_0$), i. e. $\%\delta = (E_c - E_0)/(E_{s-E0})$.

TABLE 2

Electrophoretic Mobility, Ellipticity & HIC Retention Time of 0.12 mg/mL Insulinotropin at various TWEEN® 20 Concentrations (pH 9.0, 32° C. in 10 mM sodium borate)

| TWEEN® 20 | | Ellipticity (mean residue) (222 nm) | | HIC Retention Time | | Electrophoretic Mobility cm²/Vs | |
|---|---|---|---|---|---|---|---|
| mg/mL | mM | Raw Value | % δ | min. | % δ | × 10⁻⁴ | % δ |
| 0 | | −5010 | 0 | 10.1 | 0 | −1.06 | 0 |
| 0.15 | 0.133 | −5641 | .11 | | | −1.05 | 0.02 |
| 0.30 | 0.266 | −6252 | .21 | | | −1.01 | 0.09 |
| .58 | 0.515 | −6553 | .26 | | | −1.00 | 0.11 |
| 1.13 | 1.00 | −7050 | .35 | | | −0.89 | 0.32 |
| 1.5 | | | | 9.4 | 0.11 | | |
| 1.88 | 1.67 | −7857 | .49 | | | | |
| 2.57 | 2.28 | | | | | −0.73 | 0.62 |
| 2.91 | 2.56 | −7915 | .50 | | | | |
| 3.00 | 2.66 | −8970 | .68 | 6.4 | 0.59 | | |
| 4.50 | 4.00 | −9165 | .71 | | | | |
| 5.0 | 4.44 | | | | | −0.62 | 0.83 |
| 5.63 | 5.00 | −9124 | .70 | | | | |
| 6.0 | | | | 4.8 | 0.84 | | |
| 7.95 | 7.04 | −10288 | .90 | | | | |
| 8.18 | 7.26 | −9702 | .80 | | | | |
| 10.0 | 8.88 | | | 3.8 | 1.00 | −0.61 | 0.85 |
| 10.6 | 9.41 | −10451 | .92 | | | | |
| 13.9 | 12.3 | −10540 | .94 | | | | |
| 15.0 | 13.3 | | | | | −0.55 | 0.96 |
| 19.9 | 17.7 | −10709 | .97 | | | | |
| 20.0 | | | | | | −0.58 | 0.91 |
| 22.5 | 20.0 | −10876 | 1.00 | | | | |
| 24.9 | 22.1 | −10872 | 1.00 | | | | |
| 25.0 | | | | | | −0.53 | 1.00 |

TABLE 3

Electrophoretic Mobility, Ellipticity & HIC Retention Time of 0.12 mg/mL Insulinotropin at various TWEEN® 20 Concentrations pH 3.5, 32° C. in 10 mM sodium chloroacetate)

| TWEEN® 20 | | Ellipticity (mean residue) (222 nm) | | HIC Retention Time | | Electrophoretic Mobility cm²/Vs | |
|---|---|---|---|---|---|---|---|
| mg/mL | mM | raw | % δ | min. | % δ | ×10⁻⁴ | % δ |
| 0 | 0 | −4877 | 0 | 57.6 | 0 | −1.8 | 0 |
| 0.15 | 0.133 | −7087 | 0.21 | | | −1.72 | 0.10 |
| 0.30 | 0.266 | −8437 | 0.34 | | | −1.58 | 0.28 |
| 0.58 | 0.515 | −10956 | 0.58 | | | −1.32 | 0.61 |
| 1.13 | 1.00 | −13089 | 0.59 | | | −1.14 | 0.84 |
| 1.5 | | | | 25.6 | 0.60 | | |
| 1.88 | 1.67 | −14283 | 0.91 | | | | |
| 2.57 | 2.28 | −14907 | 0.96 | | | −1.08 | 0.91 |
| 3.0 | 2.66 | | | 11.5 | 0.87 | | |
| 3.60 | 3.20 | −14961 | 0.97 | | | | |
| 5.0 | 4.44 | −15266 | 1.00 | | | −1.01 | 1.00 |
| 6.0 | 5.33 | | | 6.1 | 0.97 | | |
| 7.5 | 6.66 | | | 6.0 | 0.97 | | |
| 10.0 | 8.88 | | | 4.4 | 1.00 | | |

Both sets of experiments showed the same general trend. As the concentration of TWEEN® 20 increases, the HIC retention time decreases. Similarly, as the HIC retention times decreases, the ellipticity decreases while the electrophoretic mobility increases.

These data provide a general correlation of ellipticity and electrophoretic mobility to HIC, ie, when other variables are held constant, decreases in ellipticity or increases in electrophoretic mobility indicate decreasing HIC column retention times.

Example 2

HIC Retention Time, Electrophoretic Mobility & in vitro Skin Flux for Various Agents Three proteins were tested under similar conditions to show a correlation between protein hydrophobicity, as measured by HIC retention times, and in vitro skin flux. The proteins tested were cytochrome C, lysozyme, and ribonuclease. No surfactants were used in this study.

The in vitro skin fluxes were obtained with an aqueous donor solution of each of the three proteins with 10 mM ionic strength histidine buffer at 32° C. The receptor solution was 150 mM sodium chloride with 10 mM sodium phosphate pH 7. The pH of the donor solution for the ribonuclease was 6 while those for the cytochrome C. and lysozyme solutions were 7.

The values obtained for HIC retention times, electrophoretic mobilities and the in vitro skin fluxes for cytochrome C, lysozyme, and ribonuclease are reported in Table 4 below.

TABLE 4

HIC Retention Times, Electrophoretic Mobilities and in vitro Skin Fluxes for Cytochrome C, Lysozyme & Ribonuclease

| | Cytochrome C | Lysozyme | Ribonuclease |
|---|---|---|---|
| Molecular Weight (g/mol) | 12,400 | 14,315 | 13,686 |
| HIC Retention Time (min) (Phenyl Superose Col.) | 2.0 | 24.0 | 12.1 |
| Electrophoretic Mobility ($cm^2$/V-s) | $2.5 \times 10^{-4}$ | $2.4 \times 10^{-4}$ | $1.9 \times 10^{-4}$ |
| in vitro Skin Flux ($\mu g/cm^2$-hr) | 35 ± 10 | <1 | 30 ± 20 |

The molecular weights, sizes, charges, and electrophoretic mobilities for cytochrome C and lysozyme are similar. Their in vitro skin fluxes, however, vary substantially. A most significant difference between these compositions is their hydrophobicity, as measured by HIC retention time. The results indicate that the compositions having lower HIC retention times have higher in vitro transdermal delivery rates. Ribonuclease, for instance, has a lower HIC retention time and electrophoretic mobility than lysozyme. This combination accounts for its increased in vitro flux over that of lysozyme.

Upon analyzing these data, in conjunction with the correlation of ellipticity and electrophoretic mobility as described above, a general correlation between ellipticity or electrophoretic mobility and peptide agent transdermal flux became apparent. More specifically, this correlation may be summarized as follows. As the hydrophobicity of an agent, such as a polypeptide, decreases and its electrophoretic mobility increases, the transdermal flux of the agent tends to increase.

Example 3

Effect of Non-Ionic Surfactant on the Ellipticity of Agent

The measurement procedures described earlier were conducted on an aqueous solution of insulinotropin as the agent, and TWEEN® 40 (molecular weight 1282 g/mol) as the surfactant with the following changes. The insulinotropin concentration was initially 0.29 mg/mL, and 0.21 mg/mL after the final TWEEN® 40 addition and the temperature was held at 32° C. Two tests were conducted at two different concentrations of TWEEN® 40. One test was conducted in 10 mM sodium glycylglycinate at pH 9.0 while another was conducted in 10 mM sodium chloroacetate at pH 3.5. Table 5 below shows the ellipticity values obtained as a function of the TWEEN 40 concentration. Similar values were obtained for the earlier conditions.

TABLE 5

Insulinotropin Ellipticity at various TWEEN ® 40 Conc. (32° C., pH 3.5 in 10 mM sodium chloroacetate)

| TWEEN ® 40 Conc. | | Ellipticity (mean residue at 222 nm in |
|---|---|---|
| mg/mL | mM | deg-$cm^2$/dmol) |
| 0 | 0 | −4621 |
| 0.032 | 0.025 | −4997 |
| 0.118 | 0.092 | −6045 |
| 0.274 | 0.214 | −7317 |
| 0.500 | 0.390 | −8554 |
| 0.920 | 0.718 | −10379 |
| 1.55 | 1.21 | −12282 |
| 2.64 | 2.06 | −14017 |

This example shows a significant decrease in ellipticity produced by a non-ionic surfactant such as TWEEN®40 (resulting from detergent binding). As illustrated in the above examples, all decreases in ellipticity consistently correlate with decreases in hydrophobicity. This further demonstrates the advantage of using a non-ionic surfactant to increase the transdermal flux of agents, such as polypeptides, having hydrophobic sites.

Example 4

Effect of Ionic Surfactant on Electrophoretic Mobility & Ellipticity of a Polypeptide (Comparative Example)

The measurement procedures described earlier were conducted in this example on an aqueous solution containing insulinotropin as the agent and dodecyl trimethyl ammonium chloride (DTAC) as the ionic surfactant with the following modifications. The temperature was initially about 32° C., the pH was 3.5, and the DTAC concentration was 0.12 mg/mL in 10 mM sodium chloroacetate. Table 6 lists ellipticity and electrophoretic mobility as a function of DTAC concentration.

TABLE 6

Electrophoretic Mobility & Ellipticity of 0.12 mg/mL Insulinotropin at various DTAC concentrations (pH 3.5, 32° C. in 10 mM sodium chloroacetate)

| DTAC Conc. (mM) | Ellipticity (mean residue at 222 nm in deg-$cm^2$/dmol)) | Electrophoretic Mobility (Average) ($cm^2/V\text{-}s \times 10^{-4}$) |
|---|---|---|
| 0 | −4268 | 1.80 |
| 0.83 | −5182 | 1.82 |
| 1.64 | −7285 | 1.81 |
| 3.23 | −9863 | (1.40 to 1.90) |
| 5.51 | −11672 | (1.22 to 2.36) |
| 9.10 | −11951 | (2.94 to 4.08) |

TABLE 6-continued Electrophoretic Mobility & Ellipticity of 0.12 mg/mL
Insulinotropin at various DTAC concentrations (pH 3.5,
32° C. in 10 mM sodium chloroacetate)

| DTAC Conc. (mM) | Ellipticity (mean residue at 222 nm in deg-cm²/dmol)) | Electrophoretic Mobility (Average) (cm²/V-s × 10⁻⁴) |
|---|---|---|
| 13.0 | −12219 | |
| 15.0 | | (3.14 to 4.58) |
| 20.0 | | 3.46 |
| 25.0 | −12326 | 3.33 |

The ellipticity decreases elicited by the ionic surfactant DTAC are substantially less significant than those obtained with corresponding concentration of the polyoxyethylenes (TWEEN® 20 & 40) of Examples 1 and 2. In other words, significantly lower concentrations of non-ionic surfactants than of ionic surfactants are required to produce similar ellipticity values. For example in the case of non-ionic surfactants, an ellipticity of −9000 occurs at less than 0.3 mM with TWEEN® 20 and at less than 0.5 mM with TWEEN® 40. In contrast, in order to achieve a −9000 ellipticity for ionic surfactants, a concentration of about 3.0 mM DTAC is required. Non-ionic surfactants are, therefore, substantially superior when compared with ionic surfactants for the transdermal delivery of some polypeptides.

Example 5

Effect of Zwitterionic Surfactant on Ellipticity, Electrophoretic Mobility and HIC Column Retention Time of Agent The same measurement procedures were conducted using an aqueous solution of salmon calcitonin as the agent and the zwitterionic dodecyl sulfobetaine as the surfactant with the following modifications. The temperature was initially 32° C., the surfactant concentration was varied up to 30 mM, and the calcitonin concentration was 0.06 to 0.08 mM. Tables 7, 8, and 9 below provide the results obtained in terms of polypeptide ellipticity expressed as a function of zwitterionic surfactant concentration at pH 3.5 in 12 mM sodium chloroacetate (Table 7), 5.0 in 4 mM piperazine HCI (Table 8), and 6.5 in 15 mM sodium cacodylate (Table 9), respectively. Table 8, in addition, provides the results obtained on electrophoretic mobility and HIC retention time in a phenyl superose column at pH 5.0.

TABLE 7

Salmon Calcitonin Ellipticity vs Sulfobetaine Conc.
(32° C., pH 3.5, 12 mM sodium chloroacetate)

| Salmon Calcitonin Conc. (mM) | Dodecyl Sulfobetaine Conc. (mM) | Ellipticity (mean residue at 222 nm in deg-cm²/dmol) |
|---|---|---|
| 0.087 | 0 | −4052 |
| 0.085 | 2.44 | −4270 |
| 0.083 | 4.76 | −7984 |
| 0.082 | 5.52 | −8744 |
| 0.081 | 6.25 | −9436 |
| 0.080 | 7.69 | −10475 |
| 0.079 | 9.09 | −11072 |
| 0.078 | 10.4 | −11460 |
| 0.076 | 13.0 | −11924 |
| 0.073 | 15.5 | −12070 |
| 0.069 | 21.1 | −12285 |
| 0.063 | 27.7 | −12133 |

Clearly, increased concentrations of a zwitterionic surfactant produce a significant decrease in the ellipticity of the agent.

TABLE 8

Salmon Calcitonin Ellipticity vs Sulfobetaine Conc.
(32° C., pH 5.0, 4 mM piperazine-HCl)

| Salmon Calcitonin Conc. (mM) | Dodecyl Sulfobetaine Conc. (mM) | Electrophoretic Mobility (× 10⁻⁴ cm²/V-sec) | HIC Column Retention Time (min.) | Ellipticity (Mean Residue at 222 nm in deg-cm²/dmol) |
|---|---|---|---|---|
| 0.076 | 0 | 2.4 | 9.4 | −3919 |
| 0.076 | 0.83 | 2.3 | 12.4 | −3950 |
| 0.075 | 1.64 | 2.2 | | −4011 |
| 0.074 | 3.23 | 2.2 | 87.1 | −5209 |
| 0.073 | 4.76 | | | −7108 |
| 0.072 | 6.25 | 1.7 | 64.1 | −8348 |
| 0.071 | 7.69 | 1.5 | | −9127 |
| 0.069 | 9.77 | 1.6 | 45.1 | −9915 |
| 0.067 | 12.4 | 1.4 | | −10469 |
| 0.062 | 18.4 | 0.96 | 28.8 | −10999 |
| 0.056 | 26.4 | 0.88 | 24.4 | −11188 |
| 0.049 | 35.8 | | | −11051 |

Table 8 above shows decreased electrophoretic mobility and ellipticity as well as increased HIC retention time of the agent with higher concentrations of the zwitterionic surfactant at pH 5.0.

TABLE 9

Salmon Calcitonin Ellipticity vs Sulfobetaine Conc.
(32° C., pH 6.5, 15 mM sodium cacodylate)

| Salmon Calcitonin Conc. (mmol/l) | Dodecyl Sulfobetaine Conc. (mmol/l) | Ellipticity (mean residue at 222 nm in deg-cm²/dmol) |
|---|---|---|
| 0.071 | 0 | −4569 |
| 0.070 | 3.28 | −6725 |
| 0.068 | 6.45 | −10182 |
| 0.067 | 9.52 | −11095 |
| 0.066 | 12.5 | −11386 |
| 0.064 | 18.2 | −11744 |
| 0.061 | 28.6 | −11862 |
| 0.056 | 42.1 | −11844 |

These results demonstrate a significant decrease in the ellipticity of the agent when the zwitterionic surfactant concentration is increased.

Example 6

In vivo Administration of Agent with Enhancer and in the Absence of Enhancer (by Passive and Electrotransport Delivery)

This study was undertaken to assess the effect on the transdermal delivery rate by electrotransport of an agent such as calcitonin (sCT), a protein with an affinity for the surfactant Tween 20 at pH 6.5, by delivering the agent in the presence of Tween 20 from a donor gel.

Preparation of Electrode Matrices

A customized electrotransport system, and its reservoir matrices and contents were prepared as described below. A low level current of 100 $\mu$A cm$^{-2}$ was maintained throughout each test by a self contained power module (ALZA Corp., Palo Alto, Calif., Code #84166). The peptide agent salmon calcitonin (sCT, UCB-Bioproducts S.A., Chemin du Foriest, Allend, Belgium) was chosen for delivery by electrotransport. The protein calcitonin has a positive net charge at pH 6.5 and was therefore anodically driven from the positive electrode toward the negative electrode. Three gels were prepared for use with the electrotransport system. The anode gel provided the proper environment for the anodic electrochemical reaction. It was comprised of Bio-Rad resin beads (100–200 mesh, chloride form, Bio-Rad Laboratories, Richmond, Calif.) in 48 mM histidine buffer, pH 6.5, and 0.5% hydroxyethyl cellulose (HEC). The cathode gel provided the proper environment for the cathodic electrochemical reaction and completed the electrical circuit. It was comprised of an L-histidine buffered HEC gel, pH 2.9, and sodium chloride. The donor gel occupied a surface area of 2 $cm^2$ and was separated from the anode compartment by a 1 Kdalton molecular weight (MW) cut-off membrane (Millipore Corp., Bedford, Mass.). The donor gel was prepared by first mixing 48 mM histidine buffer, pH 6.5, with HEC, vortexing vigorously to completely dissolve the HEC and to ensure homogeneous polymerization of the gel. After a few minutes, either a 10% solution of Tween 20 (Pierce, Rockford, Ill.) or water was added in conjunction with a stock solution of calcitonin and gently mixed into the gel. The amounts of each component were calculated to produce a nominal concentration of 1 mM sCT in a 1% HEC gel of 1 mL volume (with or without Tween 20). The gel was slowly rotated and allowed to equilibrate overnight at 4° C. An aliquot of 275–295 µL of donor gel was weighed and placed in the donor reservoir of the electrotransport system immediately prior to beginning each experiment. The 3 gels were contained in 2 separate structures, with each gel compartment being a punched double-sided adhesive foam ring 0.081 cm (0.032") thick with an outside diameter of 3.2 cm (1¼") and an inside diameter of 1.6 cm (⅝"). The compartment ring containing the cathode gel was open on the skin side. The back side was covered by an electrode sandwich consisting of a 3.2 cm (1¼") diameter release liner cover, a 2.2 cm (13/15") diameter punch of electrical conducting adhesive tape, a 11 cm (4½") silver wire that was slightly coiled at one end, with the coil placed at the center of the electrode leading out, and a 1.6 cm (⅝") diameter punch of AgCl PIB electrode film. The donor gel compartment was also open on the skin side, but the back side was covered by a 2.2 cm (13/15") diameter punch of a 1,000 Dalton MW cut-off membrane. The anode compartment was then stacked on top of the donor compartment and covered with an electrode sandwich identical to the cathode, except that the AgCl PIB electrode film was replaced with a 0.025 mm thick silver (Ag) foil (Johnson Mathey Catalog Co., Ward Hill, Mass.). Both the cathode and the donor compartments also included adhesive washers (In Vivo Metric, Healdsberg, Calif.) with an outside diameter of 3.2 cm (1¼") and an inside diameter of 1.6 cm (⅝") between the skin and the bottom of the compartment to improve skin adhesion. All components of the system were punched out in advance and assembled on the day of the experiment.

Animal Preparation

Male hairless guinea pigs ("HGP", IAF/HA-HO, Charles River Breeding Laboratories, Wilmington, Mass.) were fasted overnight (17 hours), and weighed between 320 and 450 grams fasting body weight. All animals were quarantined for seven days prior to the tests to ensure their healthy state.

The animals were anesthetized with sodium pentobarbital (Anthony Product Co., Arcadia, Calif., 32.5 mg/mL in sterile 0.9% NaCl (Travenol Laboratories Inc., Deerfield, Ill.), injected intraperitoneally). Anesthesia was maintained with booster doses of diluted pentobarbital (0.05 to 0.1 mL), which was injected into an 18 cm long PE10 catheter (Clay Adams, Parsippany, N.J.) inserted into the animal's peritoneal cavity. The animals received left carotid catheters to the aortic arch (PE50 tubing (Clay Adam, Division of Beckton Dickinson and Co., Parsippany, N.J.), heat modified to form a small bump in its surface about 3 cm from a beveled insertion end) in acute, non-survival surgery, and were maintained in an anesthetized state for the entire experiment. The animals were washed thoroughly on both flanks with dilute Ivory soap, rinsed with water, dried with gauze and arranged on a heating pad. Blood samples were collected into heparinized (Elkins-Sinn, Inc., Cherry Hill, N.J.) 1.5 mL microfuge tubes by removing the syringe and needle, allowing the saline to clear from the catheter and then filling a tube with the whole blood.

A total of 18 hairless guinea pigs (HGP) were utilized in this example, which were divided into 3 groups.

(1) Test Group

Six animals were administered, by active electrotransport, calcitonin (1 mM) as a therapeutic agent and Tween 20 as the enhancer from a donor gel.

(2) Control Group A

A second group of 6 animals was administered the agent without Tween 20 from a donor gel by active electrotransport. The conditions were similar to (1) above, except for the absence of the enhancer.

(3) Control Group B

A third group of 6 animals was administered the agent by passive (ie, non-electrically assisted) transport from gels with Tween 20 as the enhancer (3 animals), and without Tween 20 (3 animals). This control group administered the compositions only by passive delivery (no electric current was applied).

Four animals were randomly selected and assigned to different groups for simultaneous testing on any particular day, The animals were prepared as described above, and the electrotransport systems were then assembled, anode and cathode gels were added, and the donor gel weights calculated.

Hematocrit counts were taken for all animals immediately before the application of current by the electrotransport system, when the systems were removed at the 4 hour time point, and at the last time point (6 hours). One mL of whole blood was collected before application of current by the electrotransport systems, and 0.5 mL samples were collected at various other times (0.5, 1, 2, 3, 3.5, 4, 4.25, 4.5, 5, 5.5, 6 hrs.). The electrotransport system was secured to each animal's flank and the current activated (for the active delivery systems only). For the active transport tests, the voltage and current were documented at each time point.

At the 4-hour time point, blood and hematocrits were collected and all the electrotransport systems removed. Sampling was continued for another 2 hours, and all samples were maintained on ice until they could be centrifuged (within 30 min. after collection). All plasma samples were transferred to 0.5 mL Sarstedt tubes (Sarstedt, Inc., Newton, N.C.), and stored at −20° C. until the calcitonin (sCT) concentration was determined by enzyme immunoassay (Cortecs Diagnostics Limited, Deeside, Clwyd CH5 2NT, UK).

Results

Following the application of the active electrotransport systems to the hairless guinea pigs as described above, the voltages of these systems decreased in the first few minutes of treatment, but remained fairly constant thereafter. The steady state voltage values ranged from 1.5 to 6.5 volts.

Figure 3:
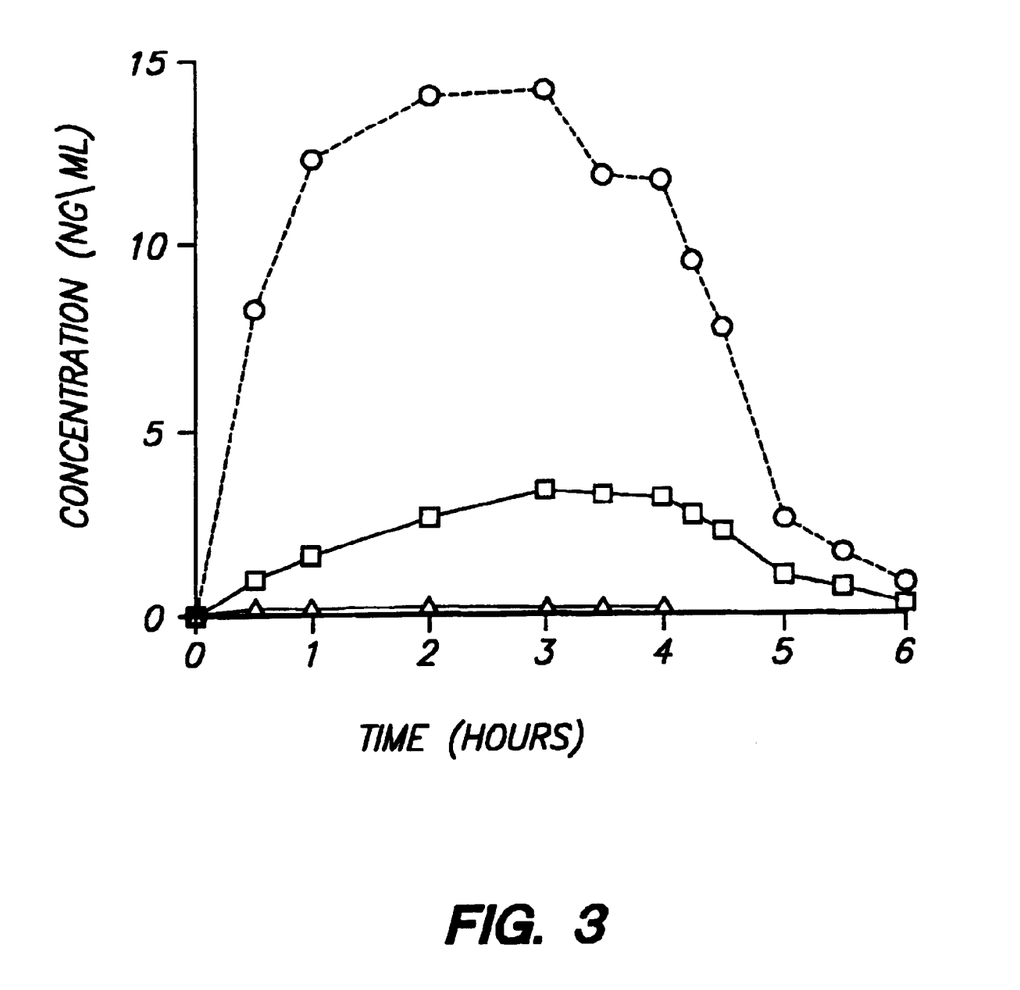
FIG. 3 shows the time variation in calcitonin plasma concentration in live hairless guinea pigs during transdermal electrotransport delivery of calcitonin under the following conditions: (1) in the presence of a surfactant enhancer (O), and (2) without a surfactant enhancer (□) in comparison to passive (ie, no applied electric current) controls (Δ).

The variation of the calcitonin plasma levels during the 6 hrs. of experimental observation for the three groups of animals is shown in FIG. 3. During the first hour of electrotransport, the calcitonin plasma concentration increased rapidly in the 2 electrotransport delivery groups, wearing the active systems and treated with current (groups (1) and (2)), whereas the calcitonin levels were low and remained at or slightly above the limit of detection in animals wearing the passive systems.

By the second hour, the two active current groups (1) and (2) approached steady state calcitonin levels. The animals in group (1), where the gel composition contained Tween 20, had an average plasma calcitonin concentration which was 3-fold that of the animals in group (2) treated with the agent but without Tween 20 (5.4 $\mu$g sCT cm$^{-2}$ h$^{-1}$ vs. 1.2 $\mu$g sCT cm$^{-2}$ h$^{-1}$). The animals in the two subgroups in control group (3) continued to lack significant calcitonin plasma levels throughout the first 4 hrs. of the test.

When a statistical significance test was applied to the results obtained for the two active transport groups of animals (groups (1) and (2)), the calcitonin plasma profiles in these two groups were found to be significantly different from one another (p<0.05, Model I analysis of variance (ANOVA), SAS 6.04).

The results obtained in this test clearly indicate a significant increase in the in vivo transdermal electrotransport in accordance with this invention of an agent such as calcitonin, in an animal model for human transdermal electrotransport, when a solid permeation enhancer such as Tween 20 is included in the donor formulation.

Example 7

In Vitro Transdermal Electrotransport Delivery of Decapeptide, Both With and Without Enhancer This study was undertaken to assess the effect of two surfactants, Tween 20 and CHAPSO (both sold by Pierce, a Prestorc Biotec Co., Rockford, Ill.) on the in vitro transdermal electrotransport delivery of the model decapeptide having the amino acid sequence shown below:

D-Glu-D-Tyr-D-Leu-D-Lys-D-Ata-D-Leu-D-Leu-D-Ser-D-Lys-D-Leu-NH$_2$.

The decapeptide has a varying hydrophobicity, as determined by the $t_a/t_m$ ratio, depending upon the pH of the donor solution and the particular buffer used. Using a 10 mM histidine (HIS) buffer at pH 6.5, the decapeptide had a $t_a/t_m$ of about 0.8. On the other hand, using a 10 mM HIS buffer at pH 7.0 the decapeptide had a $t_a/t_m$ of only 0.6 and buffered at pH 7.2 the decapeptide had a $t_a/t_m$ of only 0.5.

The aqueous receptor solution was 15 mM sodium chloride buffered to pH 7 with 10 mM imidazole. Small amounts (0.1%) of bovine serum albumin and the particular surfactant enhancer used in the experiment were added to the receptor solution to prevent the transdermally transported peptide from sticking to the glassware and other system components.

The values obtained for $t_a/t_m$ ratios, electrophoretic mobilities and in vitro skin fluxes are shown in Tables 10 and 11. Table 10 shows a composition of the present invention wherein the $t_a/t_m$ ratio is greater than 0.7. The addition of 3 mM Tween 20 resulted in an increase in transdermal electrotransport decapeptide flux of about 23%.

Table 11 shows two compositions outside the present invention since both compositions, in the absence of any enhancer, had $t_a/t_m$ ratios of less than 0.7. The addition of non-ionic surfactant (ie, 3 mM Tween 20 and 10 mM CHAPSO) to these "hydrophilic" decapeptides did not increase their transdermal electrotransport flux.

TABLE 10

$T_a/T_m$ Ratio, Electrophoretic Mobility and In Vitro Skin Flux for Model Decapeptide

| | No Enhancer | With Enhancer |
|---|---|---|
| $t_a/t_m$ | 0.8 | 0.9 |
| pH | 6.5 | 6.5 |
| Enhancer | — | 3 mM Tween 20 |
| Electrophoretic Mobility (cm$^2$/V-s) | 1.3 × 10$^4$ | 1.2 × 10$^4$ |
| in vitro Skin Flux ($\mu$g/cm$^2$-hr) | 1.3 | 1.6 |

TABLE 11

$T_a/T_m$ Ratios, Electrotransport Mobilities and In Vitro Skin Fluxes for Model Decapeptide

| | No Enhancer | With Enhancer | No Enhancer | With Enhancer |
|---|---|---|---|---|
| $t_a/t_m$ | 0.6 | 0.6 | 0.5 | 0.5 |
| pH | 7.0 | 7.0 | 7.2 | 7.2 |
| Enhancer | — | 10 mM CHAPSO | — | 3 mM Tween 20 |
| Electrophoretic Mobility (cm$^2$/V-s) | 1.2 × 10$^4$ | 0.8 × 10$^4$ | 1.1 × 10$^4$ | 1.0 × 10$^4$ |
| In Vitro Skin Flux ($\mu$g/cm$^2$-hr) | 1.7 | 1.7 | 1.5 | 1.4 |

Having thus generally described our invention and described in detail certain preferred embodiments thereof, it will be readily apparent that various modifications to the invention may be made by workers skilled in the art without departing from the scope of this invention, which is limited only by the following claims.

What is claimed is:

1. A method of delivering a therapeutic agent from an electrotransport device through a body surface comprising the steps of:

dissolving or suspending the agent and an electrotransport enhancer in a liquid solvent to provide a product, the enhancer being selected from the group consisting of nonionic surfactants and zwitterionic surfactants having substantially a zero net charge, wherein the agent has a hydrophobicity of $t_a/t_m>0.7$ as tested on a hydrophobic interaction column containing crosslinked agar beads attached to ligands by chemically stable ether linkages and having a particle size of 13.5 $\mu$m at 32° C. wherein, $t_a$ is the time at which a peak UV absorbance value occurs for a buffered solution containing the agent to flow through a hydrophobic interaction column less the time required to initially fill the column with the buffered solution containing the agent; and $t_m$ is the time at which the peak UV absorbance value occurs for a buffered solution containing N-acetyl tryptophanamide to flow through the column less the time required to initially fill the column with the N-acetyl tryptophanamide-containing buffered solution having an ionic strength of 10 mM;

wherein the column has a 5 mm diameter, a 5 cm length, and a 1.0 ml volume; and wherein the beads are constructed of SUPEROSE 12 and the ether-linked ligands are represented by —O—CH$_2$—CHOH—CH$_2$—O—R wherein R is —CH$_2$—C(CH$_3$)$_3$ or a phenyl group;

incorporating the product into a hydogel;

placing the hydrogel in agent-transmitting relation with the body surface without subjecting the hydrogel to any rehydration process; and applying an electrical current to the agent to deliver the agent through the body surface.

2. The method of claim 1, wherein $t_a/t_m > 3.0$.

3. The method of claim 1, wherein the electrotransport enhancer is present in the product in an amount sufficient to achieve a molar ratio of surfactant:agent in the range of about 3 to 10.

4. The method of claim 1, wherein the agent is selected from the group consisting of polypeptides and proteins.

5. The method of claim 4, wherein the polypeptide or protein has a net charge.

6. The method of claim 5, wherein the enhancer is a zwitterionic surfactant having a substantially neutral charge.

7. The method of claim 1, wherein the electrotransport enhancer is selected from the group consisting of polyoxyethylenes, alkyldimethylamine oxides having a pH of about 6 to 10, alkyl glucosides, alkyl maltosides, alkyl thioglucosidase, glucamides, acyl carnitines having a pH of about 6 to 8, alkyl sulfobetaines, zwitterionic bile salts, derivatives of zwitterionic salts and mixtures thereof.

8. The method of claim 1, wherein the electortransport enhancer is selected from the group consisting of polyoxyethylene (20) sorbitan monolaurate, polyoxyethylene (20) sorbitan monopalmitate, TRITON® X-100, TRITON® X-114, dodecyldimethylamine oxide having a pH above 6, decyl-β-D-glucopyranoside, nonyl-β-D-glucopyranoside, octyl-β-D-glucopyranoside, heptyl-β-D-glucopyranoside, hexyl-β-D-glucopyranoside, dodecyl-β-D-maltoside, decyl-β-D-maltoside, octyl-β-D-thioglucopyranoside, heptyl-β-D-thioglucopyranoside, digitoxin, glucamides and mixtures thereof.

9. The method of claim 1, wherein the product comprises about 0.1 to 30 wt % of the electrotransport enhancer.

10. The method of claim 1, wherein the product comprises about 10 to 20 wt % of the electrotransport enhancer.

* * * * *